United States Patent [19]

Scheie et al.

[11] Patent Number: 4,487,788
[45] Date of Patent: Dec. 11, 1984

[54] METHOD AND APPARATUS FOR TRANSFERRING THE PROFILE OF CONDITIONING MATERIAL ON A BOWLING LANE SURFACE

[75] Inventors: Carl E. Scheie, Libertyville; Howard Knoebel, Champaign, both of Ill.

[73] Assignee: Brunswick Corporation, Skokie, Ill.

[21] Appl. No.: 512,944

[22] Filed: Jul. 12, 1983

Related U.S. Application Data

[63] Continuation of Ser. No. 333,060, Dec. 21, 1981, abandoned.

[51] Int. Cl.³ .......................... B05D 3/12; G01N 1/10
[52] U.S. Cl. ........................................ 427/9; 73/864.72
[58] Field of Search ................ 156/574, 523; 118/207; 73/864.72

[56] References Cited

U.S. PATENT DOCUMENTS

| | | | |
|---|---|---|---|
| 3,074,276 | 1/1963 | Moos | 73/864.71 |
| 3,393,114 | 7/1968 | Jorgensen | 156/523 |
| 3,430,496 | 3/1969 | Swanberg et al. | 73/864.71 |
| 4,103,553 | 8/1978 | De Blasiis et al. | 73/864.71 |

OTHER PUBLICATIONS

*The Brunswick Plan for Lane Maintenance*, Brunswick Corporation, Bowling Service Department, Muskegon, Michigan, Nov. 1976.

*Primary Examiner*—Evan K. Lawrence
*Attorney, Agent, or Firm*—Wood, Dalton, Phillips, Mason & Rowe

[57] ABSTRACT

A method and apparatus for accurately transferring and permanently recording, for subsequent analysis and evaluation, the thickness and distribution of materials employed to condition a bowling lane surface. The apparatus comprises an elongated absorbent strip of transparent tape, one side of the strip adapted to absorb the conditioning materials, a roller for placing the absorbent side of the strip in pressurized contact with the conditioned bowling lane surface, and a mechanism for removing the absorbent strip from the conditioned surface of the bowling lane. Preferably, an elongated, transparent plastic backing strip is adapted to adhere to the absorbent side of the tape so as to provide a permanent record of the thickness and distribution of lane conditioning materials. The method includes the steps of pressing the absorbent side of the tape against the conditioned surface of the bowling lane removing the tape with the conditioning material absorbed thereon from the conditioned bowling lane surface, and securing the transparent plastic backing strip to the absorbent side of the tape after the tape is removed from the bowling lane to provide the permanent analyzable record.

14 Claims, 11 Drawing Figures

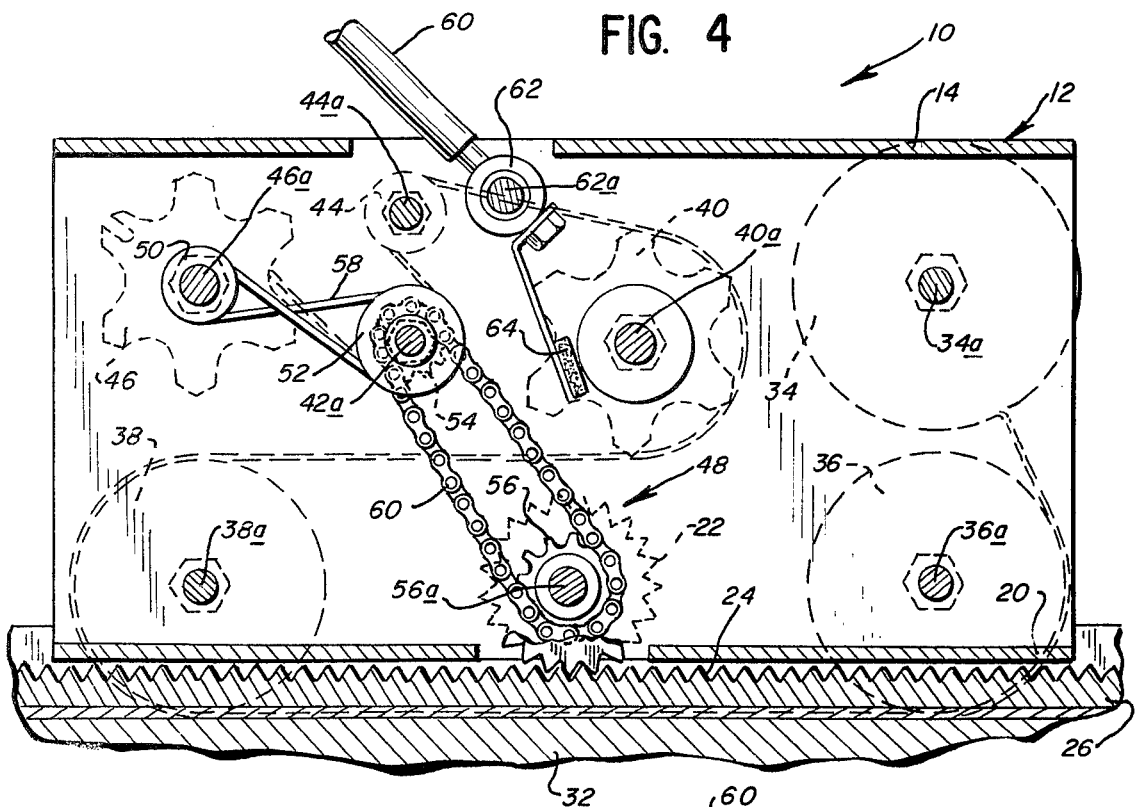

METHOD AND APPARATUS FOR TRANSFERRING THE PROFILE OF CONDITIONING MATERIAL ON A BOWLING LANE SURFACE

This application is a continuation of application Ser. No. 333,060, filed Dec. 21, 1981, abandoned.

FIELD OF THE INVENTION

This invention relates generally to a method and apparatus for determining the distribution and thickness of materials used to condition a bowling lane and more particularly relates to a method and apparatus for accurately transferring and permanently recording the thickness and distribution of conditioning material on a bowling lane surface.

BACKGROUND OF THE INVENTION

Since bowling lanes are most commonly fabricated from wood or laminated wood surfaces, they must be conditioned, i.e., treated with a liquid oil based dressing, on a daily basis to prevent the friction of a bowling ball striking and rolling along the bowling lane from scorching the surface thereof. The American Bowling Congress (ABC) requires the dressing on the lane surface to be of approximately uniform distribution. FIG. 8a is illustrative of a uniformly applied layer of lane conditioning material. FIG. 8b depicts the profile of lane conditioning material, applied pursuant to ABC specifications, but tapered to the transverse extremities of the bowling lane due to the inherent inability of the bowling lane to maintain a constant profile of conditioning material adjacent the gutters.

The ABC has discovered that many bowling center proprietors practice a technique known as "lane blocking". Lane blocking is accomplished by building-up lane conditioning materials in specified areas on a bowling lane surface to guide or steer a bowling ball into the strike "pocket" (that portion of the lane which affords the bowler the greatest opportunity of achieving a high score). Bowling center proprietors believe that the more rewarding the game of bowling is made, the more likely the bowler will return. Moreover, the ABC has a policy of checking bowling lane conditions prior to certifying individual high scores or league high scores.

Researching and testing have proven the margin of error in releasing a bowling ball to generate a strike on a properly conditioned lane, is approximately two boards (a lane is generally made of 39 one-inch longitudinally elongated boards). However, the margin of error, for releasing the ball in the appropriate strike path may be increased to as much as six boards when bowling on a blocked lane.

It is desirable that a ball delivered with side spin down a normally conditioned bowling lane surface hook into the pocket at a specific angle related to the axis of a bowling lane. With a blocked lane, where more conditioner has been placed in one portion of the lane than other portions (see FIGS. 8c and 8d which depict the profile of blocked lanes with excess conditioner applied adjacent the center area), the ball hooks in the dry areas until it contacts the more heavily conditioned portions. The heavily conditioned portions are positioned in such a way as to direct the ball into the strike pocket at said specific angle. The bowling ball will react accordingly and slide in the slippery (highly conditioned) areas and hook in high friction (minimally conditioned) areas.

Methods currently employed by the ABC to certify lane conditions are deficient. The ABC may not be able to inspect a lane immediately after a high score has been bowled, thereby providing proprietors with sufficient time to change the conditions on their lanes prior to inspection by an ABC representative.

Even in those instances in which ABC representatives arrive quickly, the ineptitude of available tests make accurate lane conditioning examination impossible. Presently only visual and smear or tactile tests are available for use by ABC representatives to determine the distribution and thickness of lane conditioner on the bowling lane surface. The visual test consists of looking at the reflection of light from the bowling lane surface; the greater the light reflected from the surface, the more conditioner has been applied to the surface.

In the smear or tactile test, the inspector slides his fingertips across the lane surface for a sensory indication of the surface feel. If the lane feels slippery, it is oily.

A "lane analyzer" is a device used to graphically demonstrate the results of the smear and tactile tests. It determines lane conditions based on the friction (the more conditioner, the less friction) encountered by a slider member placed in contact with the lane surface. Obviously, if the member slides one inch on some areas of the lane and five inches on other areas, there is a difference in friction on the lane surface. By taking readings on every board across the lane, the results can be plotted on a graph. However, the lane analyzer is not an official measuring device because readings vary when it is used on different lane finishings and with different lane dressings. Further, a heavy oil buildup in certain areas provides a "snow-plow" effect and tends to slow down the member. Therefore, when ABC personnel check lane conditions following a high score, only the smear and visual tests are available to determine if the lanes were properly conditioned. However, in these tests human judgment is a factor which renders all decisions questionable, and just as importantly, no permanent record is produced to certify the results thereof.

It is therefore the principal object of the present invention to provide an apparatus and a method to quantitatively measure the cross-sectional profile of lane conditioners applied to a bowling lane.

It is further object of the present invention to provide an apparatus and a method for transferring the lane conditioning profile onto a strip for analysis and evaluation at a later time.

It is still a further object of the present invention to provide an apparatus and a method for establishing a permanent record of the profile and distribution of conditioning materials on a bowling lane surface, the apparatus adapted to be quickly and easily set-up and the method adapted to be employed by any reasonably skilled maintenance person.

And it is yet another object of the present invention to provide an apparatus and a method for evaluating and analyzing the profile of conditioning materials on a bowling lane surface, the apparatus and method eliminating all human judgment factors.

And yet, a still further object of the present invention is to provide an apparatus and a method for determining the thickness and distribution of conditioner on a bowling lane surface, the apparatus requiring low maintenance, having simple design features and having a long, useful life.

These and other features of the present invention will become readily apparent to one of ordinary skill in the art when read in conjunction with the detailed description of the drawings and claims which follow.

While the essence of the invention described herein is the development of a suitable method for determining whether a bowling lane has been improperly conditioned and the development of hardware for transferring and recording the profile of conditioning materials applied to the surface of the bowling lane, it must be recognized that this involves only the first stage in lane analysis. To complete the lane analysis it is contemplated that the lane conditioning material be treated with a flourescent brightening additive, such as UVI-TEX OB (a Registered Trademark of the Ciba-Geigy Company) and having a maximum visible fluorescence at 435 nanometers and a maximum ultra-violet absorption at 375 nanometers. After the treated conditioner is absorbed by the absorbent strip, as described herein, the strip is analyzed under ultra-violet light. Since a relationship exists between the proportion of fluorescent brightening additive on the strip and the intensity of light emanating from the additive absorbed by the strip, the intensity of light emanation from the additive absorbed by the strip can be correlated with the thickness and distribution of the lane conditioning material on the bowling lane surface. The analysis of the strip under ultra-violet light forms the basis of another patent application, filed simultaneously herewith, of common assignment and entitled, "METHOD AND APPARATUS FOR ANALYZING CONDITIONER ON A BOWLING LANE SURFACE".

Although not specifically described, it should be apparent that the lane conditioning material could be formulated with a different type of tracer such as a metal, optically active or magnetic additive instead of the fluorescent additive described herein. The metal, optically active or magnetic additive could then be analyzed using metallic, polarized or magnetic detection equipment. Further, although photovoltaic equipment is described herein as the preferred apparatus for evaluating the lane conditioning material sample, it should be obvious that other types of evaluating apparatus such as a fluoroscope or an infra-red spectrometer could be employed without departing from the spirt and scope of the present invention. It must therefore be realized that the purpose of the present invention is to accurately transfer and permanently record, for later analysis and evaluation, the profile of conditioning material on the surface of a bowling lane. Whether that objective is accomplished with magnetic, optically active or metallic additives and regardless of the evaluation equipment employed, it is the transfer and removal equipment which forms the basis for this application.

BRIEF SUMMARY OF THE INVENTION

Disclosed herein is a method and apparatus for accurately transferring and permanently recording, for subsequent analysis and evaluation, the thickness and distribution of materials employed to condition the surface of a bowling lane. The apparatus comprises an elongated absorbent strip, preferably an adhesive-backed, transparent tape. One side of the strip is absorbent for contacting and absorbing the conditioning material applied to a bowling lane surface. The absorbent strip is wound about an absorbent strip dispensing roller from which it is directed to an absorbent strip placement roller. The placement roller has a soft circumferential edge adapted to place the absorbent strip in pressurized contact with the bowling lane surface. An elongated plastic, transparent backing strip is wound about a rotatable backing strip dispensing reel. The absorbent side of the absorbent strip is received by and adheres to the backing strip on the backing strip dispensing reel after said absorbent strip is removed from the bowling lane surface so as to prevent contamination of the absorbent side of the absorbent strip.

The absorbent strip-backing strip sandwich is then directed to a take-up reel about which the absorbent strip-backing strip sandwich is wound to facilitate handling and storage. All of the aforementioned reels and rollers are preferably mounted on a movable carriage which is adapted to traverse the bowling lane surface. To facilitate movement of the carriage across the transverse width of the bowling lane surface a rack and pinion drive assembly is provided.

The method of accurately transferring and permanently recording the profile of conditioning materials includes the steps of (1) placing the absorbent side of the absorbent strip in pressurized contact with the conditioned surface of a bowling lane, and (2) removing the absorbent strip with the conditioning materials absorbed thereon from the conditioned bowling lane surface. Additional steps may include (3) securing a transparent backing strip to the absorbent side of the absorbent strip after the absorbent strip is removed from the bowling lane surface and (4) winding the backing strip-absorbent strip sandwich onto a reel to facilitate handling and storage. The absorbent strip is thereby adapted to provide a permanent analyzable record of the thickness and distribution of the conditioning materials applied to the bowling lane surface.

BRIEF DESCRIPTION OF THE DRAWINGS

FIG. 4 is a cross-sectional view taken along line 4—4 of FIG. 1 illustrating the drive assembly of the transfer and recording apparatus;

FIG. 5 is a front elevational view of the transfer and recording apparatus of FIG. 1 with a section of the backing strip dispensing reel partially broken away to show the frictional resistance pad;

DETAILED DESCRIPTION OF THE PREFERRED EMBODIMENT

Figure 1:
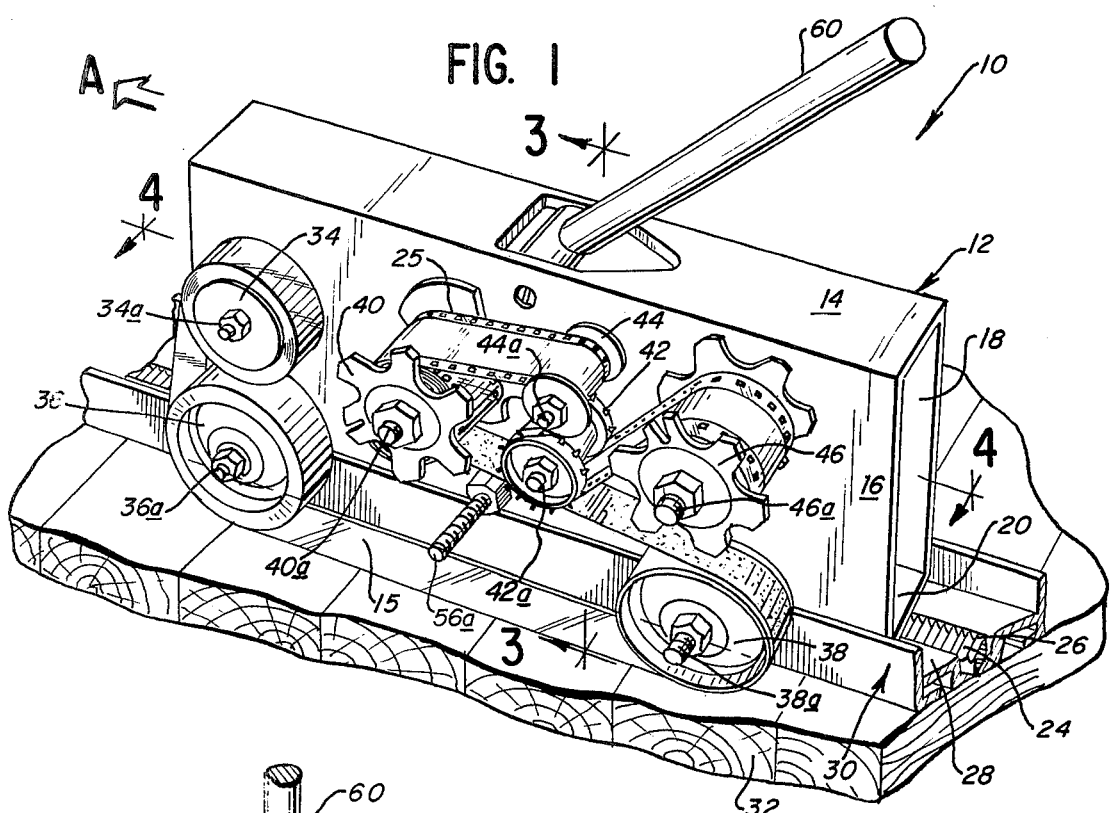
FIG. 1 is a prespective view of the transfer and recording apparatus of the present invention, the apparatus being positioned upon a fragmentary portion of a bowling lane surface.
Figures 2, 3:
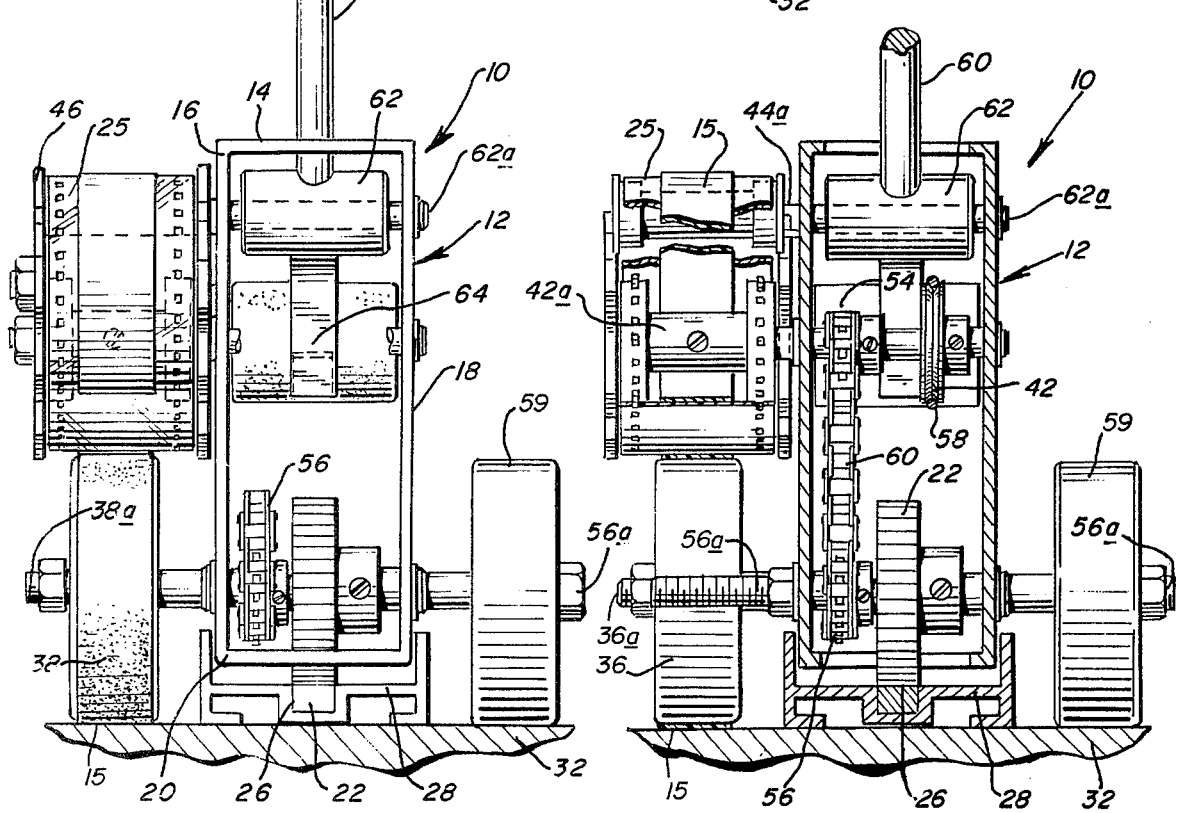
FIG. 2 is a side elevational view of the transfer and recording apparatus of FIG. 1.
FIG. 3 is a cross-sectional view taken along line 3—3 of FIG. 1 and showing further details of the drive mechanism of the transfer and recording apparatus.
Figure 6:
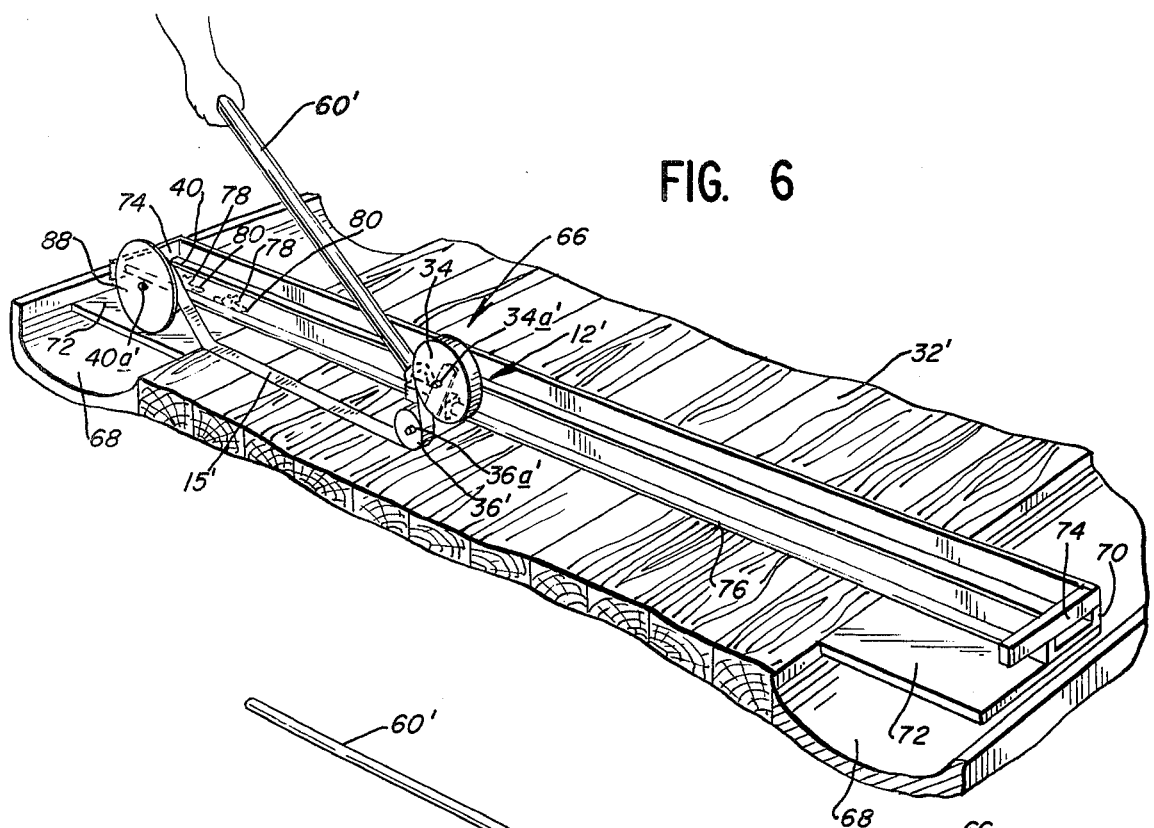
FIG. 6 is a perspective view of a second embodiment of the transfer and recording apparatus of the present invention.

Referring now to the drawings and particularly to FIGS. 1–5, the preferred embodiment of the transfer and recording apparatus of the present invention is indicated generally by the reference numeral 10. The apparatus 10 is adapted to place an absorbent strip 15, such as commercially available substantially transparent tape marketed by 3M under the Registered Trademark "SCOTCH", in contact with the surface of a bowling lane 32 and to remove said tape from said surface and onto a transparent, plastic backing strip 25, such as polyurethane, for protecting the conditioning material on the absorbent strip 15. To this end, the apparatus 10 includes a hollow, generally rectangular carriage 12, having a top surface 14, a front surface 16, a rear surface 18 and a bottom surface 20. The carriage 12 may include a pinion gear 22 extending through the bottom surface 20 and adapted to engage a rack element 24 disposed in an elongated channel 26 formed in the horizontal cross-member 28 of a generally I-shaped beam 30 which extends across the transverse width of the bowling lane surface 32. While the rack and pinion drive assembly provides a positive, non-slip drive for the transfer and recording apparatus 10, it should be readily apparent that the carriage 12 can operate without a positive drive and consequently this invention is not limited to the positive drive arrangement. Although not shown in FIGS. 1–5, the I-Beam 30 extends into the gutter areas on the sides of the lane surface 32 so as to provide a starting and stopping area for the carriage 12. To that extent the preferred embodiment is similiar to the alternative embodiment wherein, as best shown in FIG. 6, the channel 70 extends into the gutter 68 and may include a gutter platform 78.

Rotatably secured on the front face side 16 of the carriage 12 are an absorbent strip dispensing roller 34 having an axle 34a, an absorbent strip placement roller 36 having an axle 36a, an absorbent strip take-up and directing roller 38 having an axle 38a, a backing strip dispensing reel 40 having an axle 40a, a sprocketed drive roller 42 having an axle 42a, an idler roller 44 having an axle 44a, and an absorbent strip-backing strip sandwich take-up reel 46 having an axle 46a.

Rotatably secured interiorly of the hollow carriage 12 is the assembly for driving and maintaining tension between the rollers described hereinabove. The drive and tensioning assembly 48 can best be seen in FIG. 4 and includes an absorbent strip-backing strip sandwich take-up reel pulley 50 mounted on axle 46a, a drive roller pulley 52 and a drive roller gear 54 mounted on axle 42a and a pinion drive gear 56 mounted on axle 56a. A belt 58 connects drive pulleys 50 and 52 and a link chain 60 connects gears 54 and 56. Since pulley 52 and gear 54 are mounted on the same axle 42a, the absorbent strip-backing strip sandwich take-up reel 46 and the sprocketed drive roller 42 are rotated at the same rate as the pinion 22 is driven along the lane surface, the preset tension between the absorbent strip 15 and the backing strip 25 is maintained. A single carriage support wheel 59 (see FIG. 5) mounted on axle 56a extends from the lower end of the back surface 18 of the carriage 12.

Although the drive and tensioning assembly 48 has been described and illustrated as a belt and chain system, it need not be so limited. Any well-known mechanical equivalent, such as (1) a single chain connected between gear 54, gear 56 and a third gear on axle 46a (which would replace pulley 50), or (2) intermeshing gear teeth on axles 42a, 46a, and 56a could be employed to drive the rollers by an ordinary skilled artisan without departing from the spirit and scope of the invention. Also, in instances in which no pinion gear is employed, a gear could be added to axle 38a so as to drive the sprocketed roller 42 directly from roller 38. However, the illustrated drive assembly is preferred because the sprocketed drive roller 42 is rotated directly from the pinion gear 22 and the belt 58 allows slippage between the take-up reel 46 and the sprocketed roller 42 to alleviate tension which could develop in the absorbent strip-backing strip sandwich between the sprocketed roller 42 and the take-up reel 46.

In use, the carriage 12 is placed atop the I-beam 30 with the pinion gear 22 resting in the rack 24 formed in the cross-meaber 28 of the I-beam 30. When so positioned, the lower circumferential portion of the absorbent strip placement roller 36, the absorbent strip take-up and directing roller 38 and the support wheel 59 engage the surface of the bowling lane 32. A handle 60 is pivotively attached to an opening in a cylindrical body 62 for manual locomotion of the carriage 12 along the bowling lane surface 32 in the direction of arrow A in FIG. 1. As the carriage 12 is moved across the lane 32, the absorbent strip 15, which has first been threaded from dispensing roller 34 about placement roller 36 and take-up roller 38 and secured by adhesive to the backing strip 25 adjacent the backing strip dispensing reel 40, is collected on take-up reel 46. The placement roller 36 is fabricated with a soft, gum-like outer surface (having a durometer reading of about 40) so that the absorbent strip 15 is pressed downwardly onto the conditioned surface 32 to absorb all of the conditioning material therefrom.

As the carriage 12 continues to move across the surface 32, the drive and tensioning assembly 48 continues to rotate the absorbent strip-backing strip take-up reel 46. Rotation of the drive and tensioning assembly 48 winds the absorbent strip-backing strip sandwich about the absorbent strip-backing strip take-up reel 46.

By pivoting the handle 60 about axle 62a, the frictional pad 64 is brought into frictional contact with the backing strip dispensing axle 40a. Since the pad 64 only restricts rotation of the backing strip dispensing reel 40, while the take-up and directing roller 38 and the take-up reel 46 continue to rotate, play in the absorbent strip 15 or the absorbent strip-backing strip sandwich can thereby be eliminated.

Figure 7:
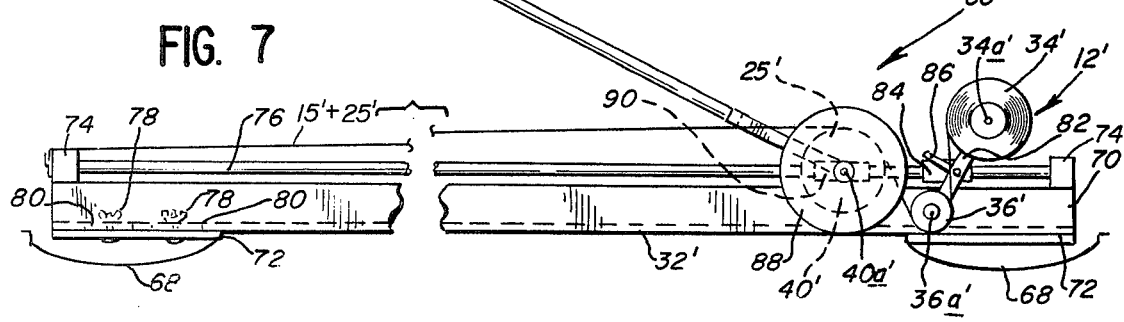
FIG. 7 is a front elevational view of the embodiment of FIG. 6 illustrating the apparatus operatively positioned between the gutters of a bowling lane.
Figure 8A:
FIG. 8a illustrates a uniform distribution of conditioning material on a surface of a bowling lane.
Figure 8C:
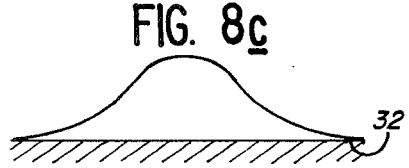
FIG. 8c illustrates one method of applying conditioning material to a bowling lane surface to block said lane.
Figure 8B:
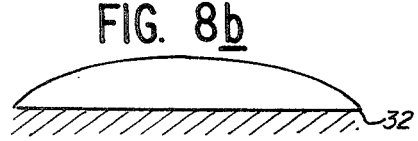
FIG. 8b illustrates an acceptable tapered distribution of conditioning material on the surface of a bowling lane.
Figure 8D:
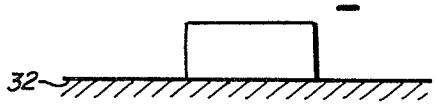
FIG. 8d illustrates a second method of applying conditioning material to a bowling lane surface to block said lane.

Turning now to FIG. 6–7, an alternate embodiment of the invention is illustrated. This alternate embodiment of the transfer and recording apparatus 66 includes a handle 60' adapted to move a roller assembly 12' across the surface of a bowling lane 32' between the gutters 68 thereof.

The transfer and recording apparatus 66 further includes an elongated, aluminum, generally U-shaped, channel 70 about fifty-eight inches in length. Since bowling lanes, such as 32', are generally forty-one and one and one half plus or minus one and one half inches in width, eight inches of the channel 70 extends into each of the gutters 68 and are used to (1) mount gutter platforms 72 on which a person operating the device may place his foot, and (2) support the bars 74 across which the slide guide rod 76 extends. The guide rod 76 enables the roller assembly 12' to be slid across the lane 32' in a straight and controlled manner.

Although, as mentioned previously, bowling lanes are about forty-one and one half inches (41½") wide, this dimension may vary slightly. Therefore, it is desirable to have one of the platforms 72 adjustable. In this embodiment, wing nuts 78 on one of the platforms 72 extend through slots 80 in the channel 70 so that said platform 72 is transversely movable until it is fitted snugly against the edges of the lane 32'.

The roller assembly 12' includes a soft rubber pressure roller 36' and an absorbent strip dispensing roller 34' which are mounted, respectively, on axles 36a' and 34a' which are secured to opposite ends of a slat 82 which is attached to an absorbent strip dispensing slider 84, see FIG. 7. The dispensing slider 84 also includes a hollow stub 86 for receiving therein one end of the handle 60'. In FIG. 6, the handle 60' is connected to stub 86 for moving the dispensing roller 34' and pressure roller 36' across the width of the lane under the guidance of rod 76.

A backing strip dispensing roller 40' is provided for dispensing a transparent, plastic backing strip 25' which is adapted for receiving the absorbent side of the absorbent strip 15' so as to protect the absorbent strip 15' from collecting extraneous substances after it is removed from the bowling lane surface 32'. A wheel 88 of larger diameter than the dispensing roller 40' is mounted on axle 40a' and is used to support the dispensing roller 40' above the lane surface 32'. The radius of the wheel 88 is equal to the distance from the centerline of the guide rod 76 to the lane surface 32'. This arrangement permits the dispensing roller 40' to rotate rearwardly, contrary to the direction of travel of the wheel 88, so that the absorbent strip 15' may be removed from the lane surface 32' and simultaneously applied to the backing strip 25'. The axle 40a' to which the dispensing roller 40' and the wheel 88 are mounted, is secured to guide bar 76 by backing strip slider 90.

In operation, the operator places the elongated, U-shaped channel 70 across the bowling lane surface 32', and adjusts the wing nuts 78 until the platforms 72 rest against the edges of the lane surface 32'. The absorbent tape 15' is pulled from the dispensing roller 34a' and placed beneath the placement roller 36', where movement of the roller assembly 12' initiated by handle 60' forces the absorbent strip 15' in pressurized contact with the lane surface 32'. The end of the absorbent strip 15' adheres to one of the bars 74 (in FIG. 7 it is the left hand bar 74) and the backing strip 25' initially is placed against and adheres to the absorbent strip 15' adjacent the bar 74. The assembly 12 is now "threaded" and ready for use.

The assembly 12' is pushed by handle 60' across the lane surface 32' until the dispensing slider 84 reaches the distal side of the lane. At this point, the absorbent strip 15' has been applied to the entire width of the lane surface 32' and absorption of lane conditioning materials, which takes only a few seconds, is complete. The handle is removed from stub 86 on slider 84 and is connected to backing strip slider 90 whereupon pushing handle 60' moves the wheel 88 and backing strip roller 40' across the lane, beneath the absorbent strip 15', to remove the absorbent strip from the lane and simultaneously apply it to the backing strip 25' as is shown in FIG. 7. The absorbent strip 15' and the backing strip 25' are both maintained in tension due to their attachment to the bar 74. When the wheel 88 and the dispensing roller 40' reach the distal end of the lane, the absorbent strip 15' is completely applied to the backing strip 25' and the absorbent strip-backing strip sandwich is suspended between the bars 74, above the lane surface.

While two forms of the invention have been described, it will be understood that the invention may be utilized in other forms and environments, so that the purpose of the appended claims is to cover all such forms of devices not disclosed but which embody the invention disclosed herein.

We claim:

1. Apparatus for accurately transferring and recording, for subsequent analysis and evaluation, the thickness and distribution of liquid materials employed to condition a bowling lane, the apparatus comprising, in combination:

an elongated, absorbent strip, one side of said absorbent strip adapted to absorb liquid conditioning materials on a bowling lane surface; and first means adapted to place the absorbent side of the absorbent strip in contact with the conditioned surface of a bowling lane; and second means for guiding the first means along a predetermined path so that a sample strip can be prepared along a length of the bowling lane.

2. Apparatus as in claim 1 further including third means adapted to remove a portion of the absorbent strip from the conditioned bowling lane surface simultaneously as said first means places a separate portion of the absorbent strip into pressurized contact with the bowling lane.

3. Apparatus as in claim 1 wherein the absorbent strip is a substantially transparent tape, said first means includes a carriage and said second means for guiding the first means comprises a channel for situation on the bowling lane surface and reception of said carriage for guiding movement therealong.

4. Apparatus as in claim 2 further including an elongated backing strip adapted to be secured to and cover the absorbent side of the absorbent strip; and fourth means adapted to secure said backing strip to the absorbent side of a portion of the absorbent strip upon the removal of the absorbent strip from the bowling lane, simultaneously as said first means places a separate portion of the absorbent strip into pressurized contact with the bowling lane, whereby the absorbent strip provides a permanent analyzable record of the thickness and distribution of the conditioning materials applied to the surface of a bowling lane.

5. Apparatus as in claim 1 further the first means for placing having a soft circumferential edge adapted to receive the absorbent strip from said absorbent strip dispensing roller, said circumferential edge being engageable with the surface of the bowling lane, said roller upon rotation moving along the bowling lane surface and pressing the absorbent side of said absorbent strip against the surface of a bowling lane.

6. Apparatus as in claim 1 wherein the backing strip is a substantially transparent material, said first means includes a slider and said second means for guiding the first means comprises a rod operably engaged with the slider for guiding movement of the first means in a straight and controlled manner.

7. Apparatus as in claim 2 wherein the third means for removing the thereabout the absorbent strip after said strip has absorbed conditioning materials from the bowling lane surface.

8. Apparatus as in claim 7 wherein the third means for removing the absorbent strip directing roller adapted to (1) pass over the non-absorbent side of the absorbent strip after said strip has absorbed conditioning materials and (2) direct said strip to the take-up reel.

9. Apparatus as in claim 8 wherein a backing strip securement means is provided and comprises a rotatable, backing strip dispensing reel having a backing strip rolled thereabout, the absorbent side of the absorbent strip adapted to be secured against said backing strip to form a sandwich, the sandwich adapted for subsequent winding about the take-up reel.

10. Apparatus as in claim 9 further including drive means for rotating the backing strip dispensing reel and the take-up reel as the directing roller passes over successive portions of the absorbent strip.

11. Apparatus for accurately transferring and permanently recording, for subsequent analysis and evaluation the thickness and distribution of liquid materials employed to condition a bowling lane, the apparatus comprising in combination:
   an elongated absorbent strip, one side of said absorbent strip adapted to absorb conditioning materials on a bowling lane surface;
   an absorbent strip dispensing roller about which the absorbent strip is wound;
   an absorbent strip placement roller adapted to receive the absorbent strip from the absorbent strip dispensing roller and press the absorbent strip against the conditioned bowling lane surface;
   an elongated backing strip adapted to be secured
   means adapted to secure said backing strip to the absorbent side of the absorbent strip to form a sandwich upon removal of the absorbent strip from the conditioned bowling lane surface; and strip-backing strip sandwich provides a permanent analyzable record of the thickness and distribution of conditioning materials applied to the surface of a bowling lane.

12. A method for accurately transferring and permanently recording, for subsequent analysis and evaluation, the thickness and distribution of liquid materials employed to condition a bowling lane; the method including the steps of:
   placing the absorbent side of an absorbent strip adapted to absorb conditioning materials on a bowling lane surface in pressurized contact with the conditioned surface of a bowling lane; and
   removing the absorbent strip with the conditioning materials absorbed thereon from the conditioned bowling lane surface, whereby the absorbent strip provides an analyzable record of the thickness and distribution of the conditioning materials applied to the surface of a bowling lane.

13. A method as in claim 12 further including the form a backing strip-absorbent strip sandwich.

14. A method as in claim 13 further including the step of winding the backing strip-absorbent strip sandwich onto a reel to facilitate handling and storage.

* * * * *